United States Patent [19]

Lodomirski

[11] Patent Number: 4,773,431

[45] Date of Patent: Sep. 27, 1988

[54] INTRA-AMNIOTIC LOOP CATHETER

[75] Inventor: Abraham Lodomirski, Narberth, Pa.

[73] Assignee: Medical Associated Services, Inc., Hatfield, Pa.

[21] Appl. No.: 21,139

[22] Filed: Mar. 3, 1987

[51] Int. Cl.$^4$ .............................. A61B 5/00
[52] U.S. Cl. ............................ 128/769; 128/361; 604/239; 604/264; 604/281
[58] Field of Search .............. 128/763, 768, 769, 770, 128/361; 604/164, 239, 264, 280, 281

[56] References Cited

U.S. PATENT DOCUMENTS

| 3,419,010 | 12/1968 | Williamson | 128/350 |
|---|---|---|---|
| 3,860,006 | 1/1975 | Patel | 128/347 |
| 3,920,023 | 11/1975 | Dye et al. | 128/347 |
| 4,033,331 | 7/1977 | Guss et al. | 128/2 M |
| 4,108,175 | 8/1978 | Orton | 128/214.4 |
| 4,117,836 | 10/1978 | Erikson | 128/2.05 R |
| 4,405,314 | 9/1983 | Cope | 604/51 |
| 4,434,803 | 3/1984 | Jeanty | 128/763 |
| 4,568,338 | 2/1986 | Todd | 604/281 |
| 4,671,795 | 6/1987 | Mulchin | 604/264 |

Primary Examiner—Edward M. Coven
Assistant Examiner—Randy Citrin
Attorney, Agent, or Firm—Benasutti & Murray

[57] ABSTRACT

An intra-amniotic loop catheter which allows direct access to a free floating segment of the umbilical cord for direct blood sampling. The loop catheter is formed of a flexible, resilient material with a distal, hook shaped end which may be straightened by an insertion or a removal tool but which returns to a hook shape when released. The hook is adapted to be oriented around a free floating section of the umbilical cord to allow insertion of a blood sampling needle into the umbilical cord through an opening in the proximal region of the hook.

2 Claims, 2 Drawing Sheets

INTRA-AMNIOTIC LOOP CATHETER

BACKGROUND OF THE INVENTION

The use of catheters in the removal of or the injection of fluids into an animal body are well known. Typically, such catheters comprise a tubular element with a central bore or lumen having a distal opening and/or longitudinal openings to the bore of the catheter. The catheter body may be rigid, semi-rigid or flexible depending upon the specific use for which it is designed.

A flexible catheter having a specific shape for use in a coronary arteriography is disclosed in U.S. Pat. No. 4,117,836. U.S. Pat. No. 4,033,331 discloses a cardiac catheter which is flexible in which the distal end has a memory or set curvature. The flexibility is controlled by a stiffening wire inserted into a lumen separate from and parallel to the main fluid lumen of the catheter.

U.S. Pat. Nos. 3,920,023 and 3,860,006 disclose flexible suprapubic catheters which include shaped ends to minimize pull-out after installation. U.S. Pat. Nos. 3,419,010 and 4,586,338 disclose flexible catheters which have distal ends with a memory for a preformed shape.

Typically, in intra-amniotic techniques such as percutaneous umbilical blood sampling (PUBS) straight, rigid needles are employed. Curent technological advances have made direct access to fetal blood during the second and third trimesters of pregnancy feasible. The ability of sample fetal blood allows more accurate prenatal fetal diagnosis and evaluation and therapy.

The existing PUBS techniques involve the insertion of a straight needle into the umbilical vessels in the region of the junction of the umbilical cord and placenta under direct ultrasonography visualization. While this procedure has an acceptable complication rate and is generally accepted, there are procedural and technical limitations. For example, with obese patients manipulation of the inserted needle in the intra-amniotic space is limited.

In some cases, fetal position or the fixation point of the umbilical cord may prevent access to the junction. In cases of oligohydramnios, the decreased amount of amniotic fluid may limit the visualization of the umbilical cord/placental junction by ultrasonographic techniques. Also, the angle of the abdominal skin level for the needle insertion may limit the manipulation of a straight needle for optimum orientation. Because of movement of the free floating umbilical cord, sampling at other than the umbilical cord/placental junction has been unknown.

SUMMARY OF THE INVENTION

The present invention provides an apparatus and method for direct fetal blood sampling from the umbilical cord with an intra-amniotic loop catheter. The intra-amniotic loop catheter of the present invention comprises a flexible catheter having a central lumen portion extending through the catheter which is formed of a flexible material. The flexible material has a memory in the shape of a hook at the distal end of the catheter. A needle is employed for insertion by placing the needle through the central lumen of the catheter to straighten the flexible hook end. The insertion needle also includes a sharp point for insertion through the uterine wall. After insertion, the straight needle is withdrawn allowing the distal end to resume its hook configuration. Under ultrasonographic visulaization, the hook can be manipulated to hold a free floating segment of the umbilical cord. A blood sampling needle may then be inserted into the central lumen of the catheter. The blood sampling needle exits the catheter through a hole in the catheter at the proximal region of the hook to enter the umbilical cord held by the hook. The catheter is removed by insertion of a straightening tool such as a stylet through the catheter lumen to straighten the hook for removal.

DETAILED DESCRIPTION OF THE PREFERRED EMBODIMENT

Figure 1:
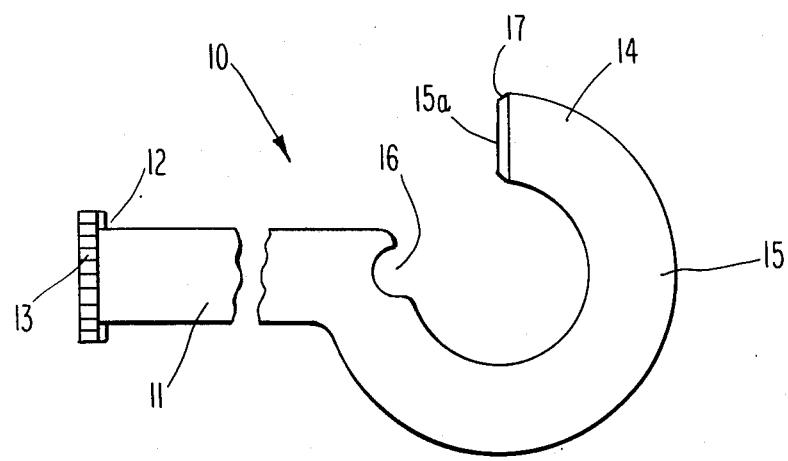
FIG. 1 is a side plan view of the loop catheter of the present invention.

The catheter 10 of the present invention comprises a tubular body 11 of a resilient flexible material. A first end 12 of the body 11 terminates in a flange 13 to facilitate manipulation of the catheter 10 and insertion of needle 20 or stylet 30 as described below. The second end 14 of the catheter 10 terminates in a hook shape 15. The hook shape 15 is permanently imparted to the catheter 10 and terminates in a distal end 15a which is opened to the central lumen 24 of the catheter 10. A sample taking opening 16 is provided in the proximal region of the hook 15 in communication with the central lumen 24 of the tubular body 11. The end surface of second end 14 of catheter 10 is beveled as at 17 to aid in insertion, described more fully below.

Figure 4:
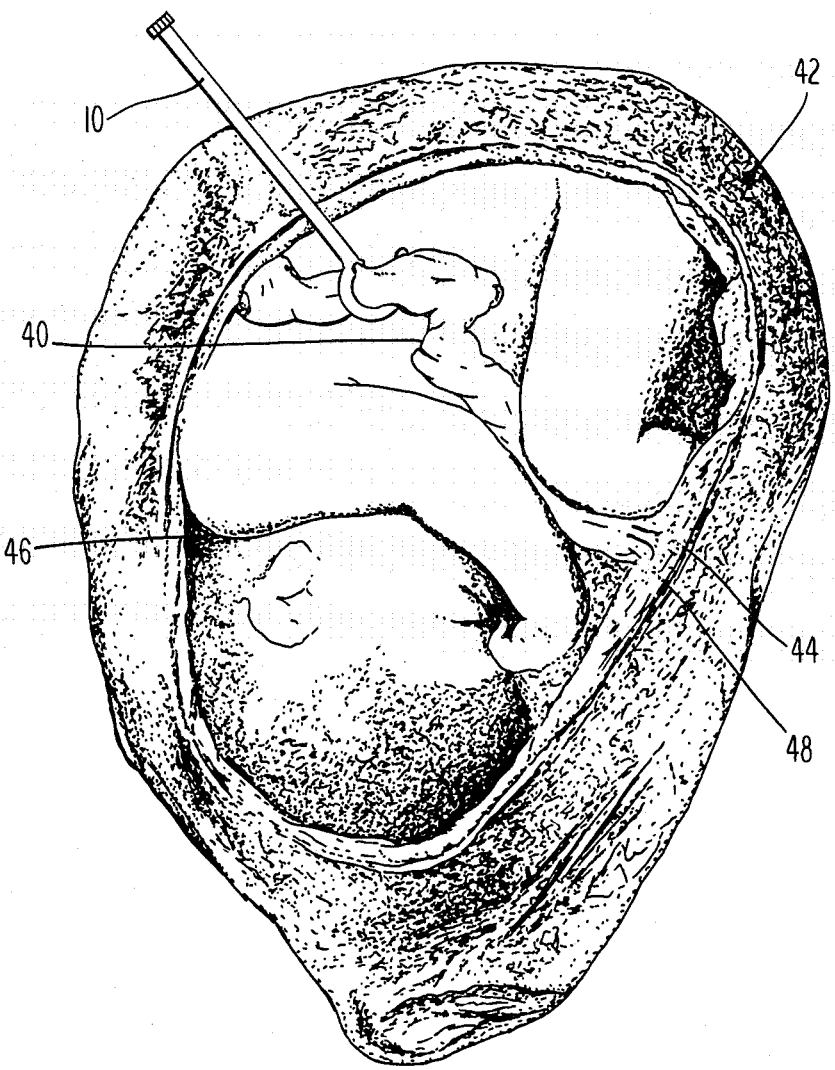
FIG. 4 shows the loop catheter of the present invention inserted into the intra-amniotic space.

The length of tubular body 11 may be easily varied to any desired length. The catheter 10 is preferably formed from a resilient flexible material which has a "memory" for the hook shape shown in FIG. 1. The flexibility of the material allows the hook shape to be deformed for insertion as described below. The catheter body 11 may be formed from the same resilient flexible material as the hook 15 or may include stiffening means (not shown) or be treated to stiffen in order to aid in manipulation of the catheter 10 after insertion. The size of hook 15 is provided to grip an umbilical cord 40 during use as shown in FIG. 4. The length of the tubular body 11 can range from approximately 8.89 cm to approximately 12.7 cm. The length used is typically a function of the size of the patient. The diameter of hook 15, adapted to surround and grip an umbilical cord is preferably equal to approximately 13 cm.

The catheter 10 is formed from a flexible material which is resilient such that it may be straightened for insertion into the amniotic cavity 46 through the uterus 42 and placenta 44. Upon release, the catheter 10 assumes the hook shape as shown in FIG. 1.

Figure 2:
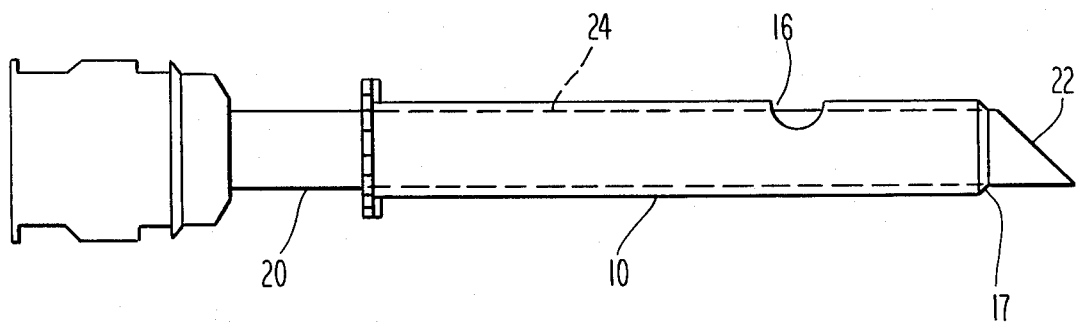
FIG. 2 is a side plan view of the loop catheter of the present invention oriented upon an insertion needle.
Figure 3:
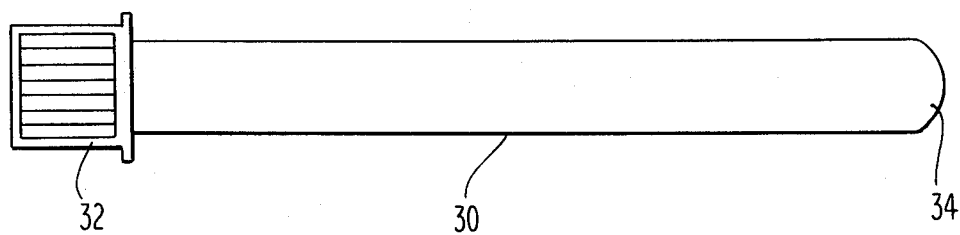
FIG. 3 is a side plan view of a removal stylet for use with the loop catheter with the present invention.

The catheter 10 is straightened for insertion by placing insertion needle 20 through lumen 24 of the catheter 10, FIG. 2. Insertion needle 20 extends completely through catheter 10 so as to expose point 22. The point 22 of the insertion needle 20 is of known configuration to pierce the skin, uterine wall 42 and placenta 44. The bevel 17 on catheter 10 aids in insertion of catheter 10 through the hole formed by insertion needle 20. Upon orientation of the catheter 10 within the amniotic cavity 46, needle 20 is removed, allowing catheter 10 to return to its normal hook shape as shown in FIG. 1. Thereafter, catheter 10 is manipulated so as to orient the hook 15 around the umbilical cord 40 with the assistance of ultrasonogrpahic visualization techniques well known in the field.

Upon orientation of the catheter 10 about the umbilical cord 40 as shown in FIG. 4, a blood sampling needle (not shown) is inserted through the central lumen 24 of catheter 10. The distal end of the blood sampling needle exits central lumen 24 through opening 16 in the proximal region of hook 15 to pierce the umbilical 40 for the taking of a blood sample. Upon removal of the blood sampling needle, catheter 10 is removed by first straightening the hook-shaped distal end by, for example, inserting a stylet 30 into the central lumen 24 thereby releasing umbilical cord 40. Stylet 30 is provided with a ribbed flange to aid in manipulation and a rounded blunt end 34 adapted to fit within central lumen 24 of catheter 10. The blunt end 34 of stylet 30 ensures that upon insertion, hook 15 is straightened and that stylet 30 does not pass through opening 16.

The intra-amniotic loop catheter of the present invention allows for direct fetal blood sampling from free floating sections of the umbilical cord obviating the need for insertion of a rigid needle into the junction of the umbilical cord and the placenta. The flexible, resilient hook portion of the catheter holds any portion of the free floating umbilical cord which may be "caught" during ultrasonographic visualization or other similar means. The use of such an amniotic loop catheter allows the doctor to move the umbilical cord away from the body of the fetus during sampling. Such direct sampling from the umbilical cord obviates the necessity for access to the umbilical cord/placenta junction as was necessary in the prior art straight needle techniques thus avoiding the necessity of any manipulation of the fetus. Further, use of the intra-amniotic loop catheter of the present invention to snare any portion of the umbilical is a less intrusive alternate to prior art fetal blood sampling techniques.

It will be understood that various changes in the details of the apparatus and its method of use, which have been described and illustrated in order to explain the nature of the present invention may be made by those skilled in the art without departing from the principle and scope of the invention as expressed in the following claims.

What is claimed is:

1. An intra-amniotic catheter for insertion into an amniotic cavity comprising: a catheter having a straight portion having a longitudinal axis and a central lumen along said axis, said catheter further having a distal end comprising a flexible resilient tubular portion in a hook shape which is adapted to hold an umbilical cord, including an opening in a region of the hook-shaped distal end proximal to the straight portion, said opening being in communication with said central lumen and substantially transverse to said longitudinal axis of said straight portion, whereby a blood sampling needle may be inserted through said opening after said hook-shaped distal end of said catheter is positioned around a segment of an umbilical cord.

2. The intra-amniotic catheter of claim 1 further including an opening in a distal end of said hook-shape to allow orientation of said catheter about an insertion needle.

* * * * *